US010314504B2

(12) United States Patent
Albadawi et al.

(10) Patent No.: US 10,314,504 B2
(45) Date of Patent: Jun. 11, 2019

(54) ELECTROCARDIOGRAM (EKG) INDICATION SATURATION CORRECTION

(71) Applicant: Microsoft Technology Licensing, LLC, Redmond, WA (US)

(72) Inventors: Haithem Albadawi, Redmond, WA (US); Chris Reidy, Redmond, WA (US); Zongyi Liu, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 73 days.

(21) Appl. No.: 15/352,321

(22) Filed: Nov. 15, 2016

(65) Prior Publication Data

US 2018/0132742 A1     May 17, 2018

(51) Int. Cl.
*A61B 5/04*       (2006.01)
*A61B 5/044*      (2006.01)
(Continued)

(52) U.S. Cl.
CPC .......... *A61B 5/04012* (2013.01); *A61B 5/002* (2013.01); *A61B 5/02416* (2013.01);
(Continued)

(58) Field of Classification Search
USPC ........................................................ 600/521
See application file for complete search history.

(56) References Cited

U.S. PATENT DOCUMENTS 7,801,593 B2    9/2010  Behbehani et al.
9,014,794 B2    4/2015  Brodnick et al.
(Continued)

FOREIGN PATENT DOCUMENTS

WO    2015153426 A1    10/2015

OTHER PUBLICATIONS

Saadi, et al., "Automatic QRS complex detection algorithm designed for a novel wearable, wireless electrocardiogram recording device", In Proceedings of 34th Annual International Conference of IEEE Engineering in medicine and biology society, Aug. 28, 2012, pp. 2913-2916.
(Continued)

*Primary Examiner* — Nicole F Lavert
*Assistant Examiner* — Nicole F Johnson
(74) *Attorney, Agent, or Firm* — Arent Fox LLP

(57) ABSTRACT

Methods and devices for correcting electrocardiogram (EKG) indication saturation may include receiving an EKG indication from at least one sensor and determining that a saturation condition has been met in response to receiving the EKG indication. Additionally, the methods and devices may include incrementing an EKG saturation level based on a determination that the saturation condition has been met. Moreover, the methods and devices may include determining whether the EKG saturation level satisfies an EKG saturation threshold. The methods and device may include disregarding at least a second EKG indication in accordance with a determination that the saturation level satisfies the EKG saturation threshold. The methods and devices may further include transmitting the second EKG indication to an output device in accordance with a determination that the saturation level does not satisfy the EKG saturation threshold.

16 Claims, 7 Drawing Sheets

(51) Int. Cl.
*A61B 5/0456* (2006.01)
*A61B 5/00* (2006.01)
*A61B 5/024* (2006.01)
*A61B 5/0424* (2006.01)

(52) U.S. Cl.
CPC ............ *A61B 5/044* (2013.01); *A61B 5/0424* (2013.01); *A61B 5/0456* (2013.01); *A61B 5/681* (2013.01); *A61B 5/7203* (2013.01); *A61B 5/6824* (2013.01); *A61B 5/6831* (2013.01)

(56) References Cited

U.S. PATENT DOCUMENTS

| | | |
|---|---|---|
| 9,078,577 B2 | 7/2015 | He et al. |
| 9,119,546 B2 | 9/2015 | Lee et al. |
| 9,414,767 B2 | 8/2016 | Speier |
| 2014/0073982 A1 | 3/2014 | Yang et al. |
| 2014/0343439 A1* | 11/2014 | Sweeney .............. A61B 5/0205 600/484 |

OTHER PUBLICATIONS

Rabbani, et al., "R Peak Detection in Electrocardiogram Signal Based on an Optimal Combination of Wavelet Transform, Hilbert Transform, and Adaptive Thresholding", In Journal of Medical Signals and Sensors, vol. 1, Issue 2, May 2011, 8 pages.

"Peak Analysis", https://in.mathworks.com/help/signal/examples/peak-analysis.html?requestedDomain=in.mathworks.com, Retrieved Date: Sep. 23, 2016, 9 pages.

Bhatti, et al., "R-Peak detection in ECG signal compression for Heartbeat rate patients at 1KHz using High Order Statistic Algorithm", In Journal of Multidisciplinary Engineering Science and Technology, vol. 2, Issue 9, Sep. 2015, pp. 2509-2515.

* cited by examiner

ELECTROCARDIOGRAM (EKG) INDICATION SATURATION CORRECTION

BACKGROUND

The present disclosure relates to electronic devices, and more particularly, to correcting electrocardiogram (EKG) indication or signal saturations at a wearable electronic device.

Use of computing devices is becoming more ubiquitous by the day. Computing devices range from standard desktop computers to wearable computing technology and beyond. The field of wearable devices has grown in recent years with the introduction of fitness bands and smart watches, some of which can interface with a nearby mobile device via short range communication technology (e.g., Bluetooth) to provide information thereto and/or to obtain and display information therefrom for consumption by a user wearing the fitness band or smart watch. These devices may include GPS systems, altimeters, and stopwatches, for example, and may track a user's speed, position and time while running, bicycling, skiing, etc.

One problem with such devices is that they typically do not present the user with accurate information other than time and position information. As such, users may connect conventional external sensors, such as non-invasive blood pressure devices to obtain biometric feedback. However, the use of multiple components in this manner may be bulky and make performance of various activities such as exercise awkward. Further, the use of other sensors such as an EKG sensor may not provide accurate EKG readings during various activities.

Thus, there is a need in the art for improvements in EKG detections in a wearable electronic device.

SUMMARY

The following presents a simplified summary of one or more implementations in order to provide a basic understanding of such implementations. This summary is not an extensive overview of all contemplated implementations, and is intended to neither identify key or critical elements of all implementations nor delineate the scope of any or all implementations. Its purpose is to present some concepts of one or more implementations in a simplified form as a prelude to the more detailed description that is presented later.

In one example, a method of resolving electrocardiogram (EKG) indication saturation at an electronic device is provided. In particular, the method may include receiving an EKG indication from at least one sensor. The method may further include determining that a saturation condition has been met in response to receiving the EKG indication. Additionally, the method may include incrementing an EKG saturation level based on a determination that the saturation condition has been met. Moreover, the method may include determining whether the EKG saturation level satisfies an EKG saturation threshold. The method may further include disregarding at least a second EKG indication in accordance with a determination that the saturation level satisfies the EKG saturation threshold. In addition, the method may include transmitting the second EKG indication to an output device in accordance with a determination that the saturation level does not satisfy the EKG saturation threshold.

In another example, an electronic device for resolving EKG indication saturation comprising a memory configured to store data and instructions, at least one sensor configured to obtain one or more sensor measurements, and a processor in communication with the memory, an output device and the at least one sensor may monitor blood pressure. The processor may be configured to receive an EKG indication from the at least one sensor. The processor may further be configured to determine that a saturation condition has been met in response to receiving the EKG indication. Additionally, the processor may be configured to increment an EKG saturation level based on a determination that the saturation condition has been met. Moreover, the processor may be configured to determine whether the EKG saturation level satisfies an EKG saturation threshold. The processor may further be configured to disregard at least a second EKG indication in accordance with a determination that the saturation level satisfies the EKG saturation threshold. In addition, the processor may be configured to transmit the second EKG indication to an output device in accordance with a determination that the saturation level does not satisfy the EKG saturation threshold.

In a further example, a computer-readable medium storing instructions executable by an electronic device for resolving EKG indication saturation. The computer-readable medium may include at least one instruction for causing the computer device to receive an EKG indication from at least one sensor. The computer-readable medium may further include at least one instruction for causing the electronic device to determine that a saturation condition has been met in response to receiving the EKG indication. Additionally, the computer-readable medium may include at least one instruction for causing the electronic device increment an EKG saturation level based on a determination that the saturation condition has been met. Moreover, the computer-readable medium may include at least one instruction for causing the electronic device to determine whether the EKG saturation level satisfies an EKG saturation threshold. The computer-readable medium may further include at least one instruction for causing the electronic device to disregard at least a second EKG indication in accordance with a determination that the saturation level satisfies the EKG saturation threshold. In addition, the computer-readable medium may further include at least one instruction for causing the electronic device to transmit the second EKG indication to an output device in accordance with a determination that the saturation level does not satisfy the EKG saturation threshold.

Additional advantages and novel features relating to implementations of the present disclosure will be set forth in part in the description that follows, and in part will become more apparent to those skilled in the art upon examination of the following or upon learning by practice thereof.

DESCRIPTION OF THE FIGURES

The specific features, implementations, and advantages of the disclosure will become better understood with regard to the following description, appended claims, and accompanying drawings where:

DETAILED DESCRIPTION

Figure 1A:
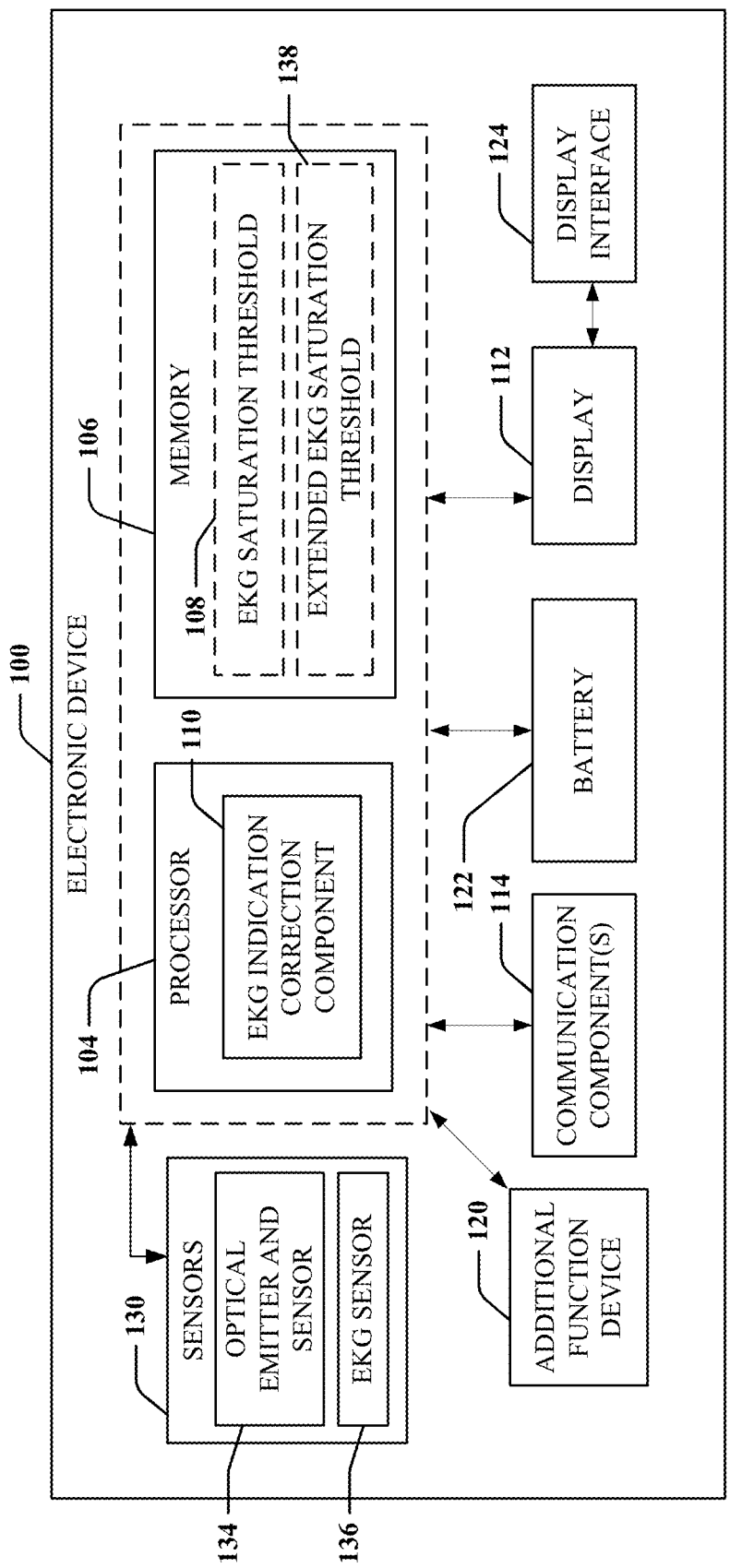
FIG. 1A is a schematic block diagram of an example electronic device including an electrocardiogram (EKG) indication correction component in accordance with some implementations.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known components are shown in block diagram form in order to avoid obscuring such concepts. In some implementations, examples may be depicted with reference to one or more components and one or more methods that may perform the actions or operations described herein, where components and/or actions/operations in dashed line may be optional.

The present disclosure relates to correcting electrocardiogram (EKG) signal or indication saturation at a wearable electronic device. For example, wearable electronic devices may be used (e.g., worn on a wrist) by a user during various activities. Such activities may include, but are not limited to, walking, running, or any other activity that may increase a heart rate of a user. Further, some wearable electronic devices may include at least an EKG sensor to measure or otherwise detect an EKG signal or indication of a user. In some implementations, an EKG indication or signal may provide a recording or measurement of the electrical activity of a heart over a period of time.

The EKG sensor of the wearable electronic device may become saturated during certain user activities. That is, the EKG sensor may detect false 'R' wave peaks corresponding to a highest detected electrical value from the overall EKG indication/signal during activities, where such false detections may alter an accurate reading of a user's EKG. However, an 'R' wave peak may be part of a number of waveforms forming an EKG indication (e.g., 'P', 'Q', 'S', and 'T'), and may specifically be an initial upward deflection after a 'P' wave that represents early ventricular depolarization. As such, each EKG indication may include at least an 'R' wave. For instance, a consistently strong heart beat and/or instances of high conductivity caused by wet or moist skin may trigger or otherwise result in EKG signal/indication saturation for periods of time.

An EKG signal/indication saturation may occur when consecutive 'R' wave peaks are detected, where a second EKG indication may be considered saturated for including a 'R' wave peak that immediately follows a previous 'R' wave peak of another EKG indication. As such, it may be beneficial to detect and correct EKG signal/indication saturation in order to avoid false 'R' wave peaks. In some applications such as wearable electronic devices, this correction may be performed in real-time. One approach for correction may be to zero out the individual EKG signals/indications corresponding to false 'R' wave peaks that are determined to be the saturated EKG signals/indications.

Nonetheless, a number of challenges may exist for the aforementioned approach. For example, if the EKG signals/indications are corrected when EKG(t)>T (e.g., with 't' being time and 'T' being a saturation threshold), then the EKG signals/indications right before t, (EKG(t−1), EKG(t−2), . . . ), may be unsaturated but may have high amplitudes as well, and may likely be falsely detected as 'R' wave peaks. Further, for instance, if the EKG signals/indications have been saturated for an extended period of time, then it may take some time for the EKG readings to settle back down to a normal or an unsaturated state. Additionally, it may be difficult to locate a clear saturation cutoff. In other words, for some users who may be very conductive, some of their true 'R' wave peaks may also appear to be saturated EKG signals/indications. Moreover, in some applications a real-time signal filter (e.g., band-pass filter, notch filter) may be applied to the EKG signal/indication to remove noise. However, such a filter may be sensitive to sharp value changes so that when a saturation is detected and corrected (e.g., value adjusted to zero), it affects the filter for a certain amount of time.

The present implementations provide a multi-tiered approach for correcting EKG signal/indication saturation based on, for instance, a length of an EKG signal/indication saturation. Specifically, a wearable electronic device may detect and correct EKG signal/indication saturation based on determining that a number of consecutive EKG signals/indications that are determined to be saturated EKG signals/indications satisfies (e.g., meets or exceeds) an EKG saturation threshold (such as, but not limited to, 10 EKG samples/signals, for instance). In some instances, an extended or prolonged number of saturated EKG signals/indications (also referred to as a "saturation event") may occur and be detected. In such a scenario, an extended EKG indication threshold may be utilized to correct for the saturated event. Specifically, the wearable electronic device may not only correct (e.g., zero or skip) a number of subsequent saturated EKG signals/indications following a determination that the extended EKG indication threshold has been met, but may also correct (e.g., zero or skip) a number of unsaturated EKG signals/indications to allow the EKG readings to settle and provide an accurate representation of the user's EKG.

Figure 1B:
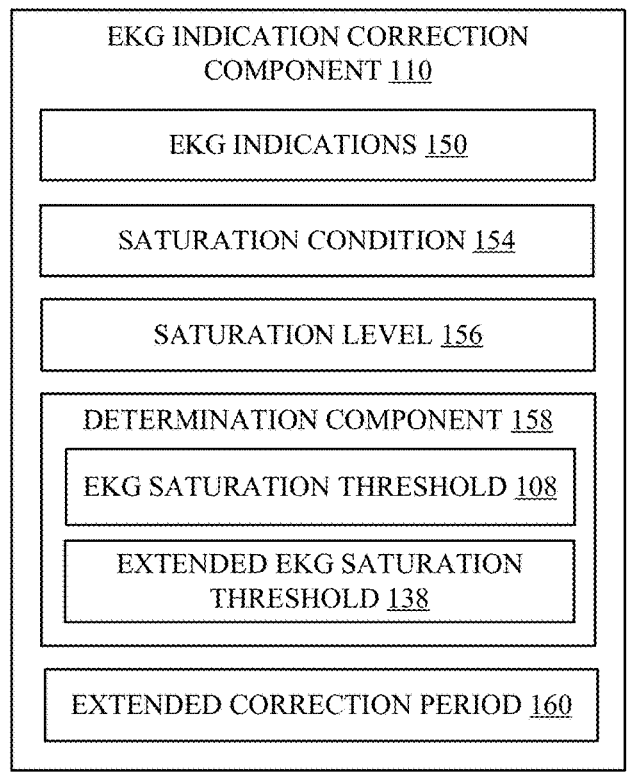
FIG. 1B is a schematic block diagram of the EKG indication correction component and various subcomponents in accordance with some implementations.

Referring now to FIGS. 1A and 1B, an example electronic device 100 may include one or more components and/or subcomponents such as an EKG indication correction component 110 for detecting and correcting one or more EKG measurements of a user of the electronic device 100. In some implementations, electronic device 100 may be or otherwise take the form of a smart watch, fitness band, and/or other wearable device. In some implementations, electronic device 100 may include or may otherwise be coupled with a processor 104 and/or memory 106, where the processor 104 and/or memory 106 may be configured to execute or store instructions or other parameters, such as blood pressure parameters 108, related to executing an EKG indication correction component 110 for detecting and correcting one or more EKG measurements of a user of the electronic device 100. For example, EKG indication correction component 110 can correspond to an operating system of the electronic device 100 (e.g., a mobile operating system) or an application executing on the operating system of the electronic device 100.

In some implementations, electronic device 100 may also include a display 112 having a presentation area, such as a screen, for presenting one or more graphical interfaces (e.g., graphical user interfaces (GUI)), such as to provide information for consumption by a user wearing the electronic device 100. For example, the display 112 may be or may include a liquid crystal display (LCD), light emitting diode (LED), organic LED (OLED), high-contrast electronic ink (E-Ink), or a fabric including light pipes, micro-LED array, and may display graphical interfaces as instructed by processor 104 (e.g., based on execution of the blood pressure determination component 110). Electronic device 100 may also include a display interface 124 that couples to display 112 to provide instructions, parameters, etc. for displaying the graphical interfaces. In some implementations, the display 112 and/or the display interface 124 may form a touch-sensitive display that may detect touch inputs on the display 112 (e.g., for interacting with a user interface) and also output data in the form of graphical representations (e.g., on the user interface).

In some implementations, electronic device 100 may also include one or more communication component(s) 114 for communicating with a computing device 140 via a wired or wireless interface (e.g., Bluetooth, radio frequency identification (RFID), near field communication (NFC)). Electronic device 100 may also include a battery 122 for providing power to various components and/or subcomponents of the electronic device 100.

In some implementations, electronic device 100 may also include one or more sensors 130, which may include an optical emitter and sensor 134 for transmitting and detecting light to and from a capillary of a user of the electronic device. The light signals/indications may be used to determine a PPG signal/indication corresponding to a heart rate of the user. Further, the one or more sensors 130 may also include an EKG sensor 136 in the form of an electrical pulse/signal sensor. For example, the EKG sensor 136 may detect an electrical signal/indication corresponding to an EKG signal based on detecting contact of at least a finger of each hand of a user with the electronic device 100.

In some implementations, the one or more sensors 130 may also include an accelerometer for detecting at least acceleration of the electronic device 100, a gyro sensor for detecting angular velocity of the electronic device 100, an angle or orientation sensor for detecting a position of electronic device 100 relative to a reference plan, a compass for determining a direction of magnetic north and bearing from it, an ultraviolet (UV) sensor for detecting light in the ultraviolet spectrum, and/or a barometer for measuring atmospheric pressure.

In addition, electronic device 100 may include one or more additional function devices 120 for providing additional functionality to the modular device core 100, such as a global positioning system (GPS) radio, a fitness tracking device (e.g., step tracking device, pulse monitor or tracking device, power meter), a battery, a microphone, a galvanic skin sensor, a memory, a processor, communication interface, such as an RFID radio, Bluetooth radio, Wi-Fi radio, etc.

In some implementations, electronic device 100 (and/or computer device 140) may include an operating system executed by processor 104 and/or memory 106 of electronic device 100. Memory 106 may be configured for storing data and/or computer-executable instructions defining and/or associated with operating system (and/or firmware), and processor 104 may execute operating system and/or one or more associated components such as blood pressure determination component 110. An example of memory 106 can include, but is not limited to, a type of memory usable by a computer, such as random access memory (RAM), read only memory (ROM), tapes, magnetic discs, optical discs, volatile memory, non-volatile memory, and any combination thereof. An example of processor 104 may include, but is not limited to, any processor specially programmed as described herein, including a controller, microcontroller, application specific integrated circuit (ASIC), field programmable gate array (FPGA), system on chip (SoC), or other programmable logic or state machine.

EKG indication correction component 110 may at least correct one or more EKG indications 150 identified as, or otherwise determined to be saturated. In particular, as part of monitoring or continuously determining a user's EKG, EKG indication correction component 110 may be configured to receive one or more indications 150 from, for example, the EKG sensor 136. As EKG indication correction component 110 receives each of one or more indications 150, which may take the form of electrical signals measured in millivolts over time by the EKG sensor 136, a determination may be made as to whether each EKG indication satisfies a saturation condition 154. That is, EKG indication correction component 110 may determine whether an EKG indication that is received from the EKG sensor 136 is saturated, which may be indicative of a false 'R' wave peak measurement caused by, for example, a strong user heartbeat and/or high conductivity at or near the EKG sensor 136. Specifically, a saturated EKG indication may be an electrical signal measured in millivolts that meets or exceeds a saturation threshold value (e.g., also in millivolts) signifying the saturation condition 154. For example, the saturation threshold may be an EKG indication including an 'R' wave peak that immediately follows a previous 'R' wave peak. The saturation threshold may be set to a voltage value in millivolts indicative of an EKG saturation level (e.g., corresponding to an 'R' peak voltage value).

In some implementations, EKG indication correction component 110 may determine whether the saturation condition 154 has been met by detecting that an EKG indication includes an 'R' peak that follows a previous EKG indication also including an 'R' peak (e.g., the saturation threshold is any EKG indication having an 'R' wave peak subsequent to any other EKG indication having an 'R' wave peak). Upon determining that the saturation condition 154 has been met for a particular EKG indication or measurement, EKG indication correction component 110 may be configured to increment a saturation level 156 from a current saturation value to a new saturation value. In some implementations, the saturation level 156 may be a value indicative of a number of saturated EKG indications received from the EKG sensor 136.

Further, upon incrementing the saturation level 156 based on determining that the saturation condition 154 has been met for the particular EKG indication, EKG indication correction component 110 may be configured to determine whether the saturation level 156 satisfies (e.g., meets or exceeds) an EKG saturation threshold 108. In some implementations, the EKG saturation threshold 108 may correspond to a minimum number of saturated EKG indications sufficient for triggering a correction of at least one EKG indication (e.g., when saturation level 156 meets or exceeds the minimum number of saturated EKG indications). In a non-limiting example, the EKG saturation threshold 108 may correspond to 5-15, 8-12, 9-11, or 10 saturated EKG indications/signals.

Upon determining that the saturation level 156 satisfies (e.g., meets or exceeds) the EKG saturation threshold 108, EKG indication correction component 110 may correct subsequent saturated EKG indications. In some implementations, by correcting the saturated EKG indications, EKG indication correction component 110 may be configured to adjust a value of a saturated EKG indication from a saturated value (e.g., indicative of a false 'R' wave peak) to zero (alternatively referred to as 'zeroing'). For example, EKG indication correction component 110 may zero the saturated EKG indications by disregarding or skipping the saturated EKG indications that are detected or otherwise received after determining that the saturation level 156 satisfies the EKG saturation threshold 108.

If EKG indication correction component 110 determines that the saturation level 156 does not satisfy the EKG saturation threshold 108, EKG indication correction component 110 may be configured to forego correcting the EKG indication and/or transmit the EKG indication to display 112 (or another component/subcomponent of electronic device 100) for presentation to the user. That is, although EKG indication correction component 110 detected a saturation condition 154 associated with the particular EKG indication, EKG indication correction component 110 nonetheless may not correct (e.g., 'zero') the saturated EKG indication as it may be within an acceptable range of accurate or typical EKG measurements/patterns.

Additionally, EKG indication correction component 110 may be configured to determine whether the saturation level 156 satisfies an extended EKG saturation threshold 138. For example, the extended EKG saturation threshold 138 may correspond to an extended number of saturated EKG indications sufficient for triggering a correction of at least one saturated EKG indication and at least one unsaturated EKG indication. In other words, upon determining that the saturation level 156 satisfies the extended EKG saturation threshold 138, EKG indication correction component 110 may be configured to not only correct (e.g., 'zero') subsequent saturated EKG indications following the EKG indication that incremented the saturation level 156 to a value that satisfied the extended EKG saturation threshold 138, but also subsequent unsaturated EKG indications for an extended correction period 160 (e.g., in the form of a number of EKG indications/signals or a time duration during which any unsaturated EKG indication/signal is received). In some implementations, the extended EKG saturation threshold 138 may be greater than the EKG saturation threshold 108.

Upon an expiration of the extended correction period 160, EKG indication correction component 110 may be configured to cease correction or 'zeroing' of the unsaturated EKG indications/signals, and transmit the unsaturated EKG indications to the display 112 (or another component/subcomponent of electronic device 100) for viewing by a user of electronic device 100. For example, display 112 of the electronic device 100 may be configured to receive and display an EKG value associated with an EKG indication or measurement from EKG indication correction component 110. Display 112 may be configured to receive and display, in real-time, one or more EKG values over a time duration that the EKG sensor 136 obtains the EKG indications 150, and the EKG indication correction component 110 corrects or resolves any false 'R' wave peaks. Further, for example, during the extended correction period 160, display 112 may be configured to display a zero value corresponding to the EKG indications 150 determined to be 'zeroed' by EKG indication correction component 110.

Figure 2:
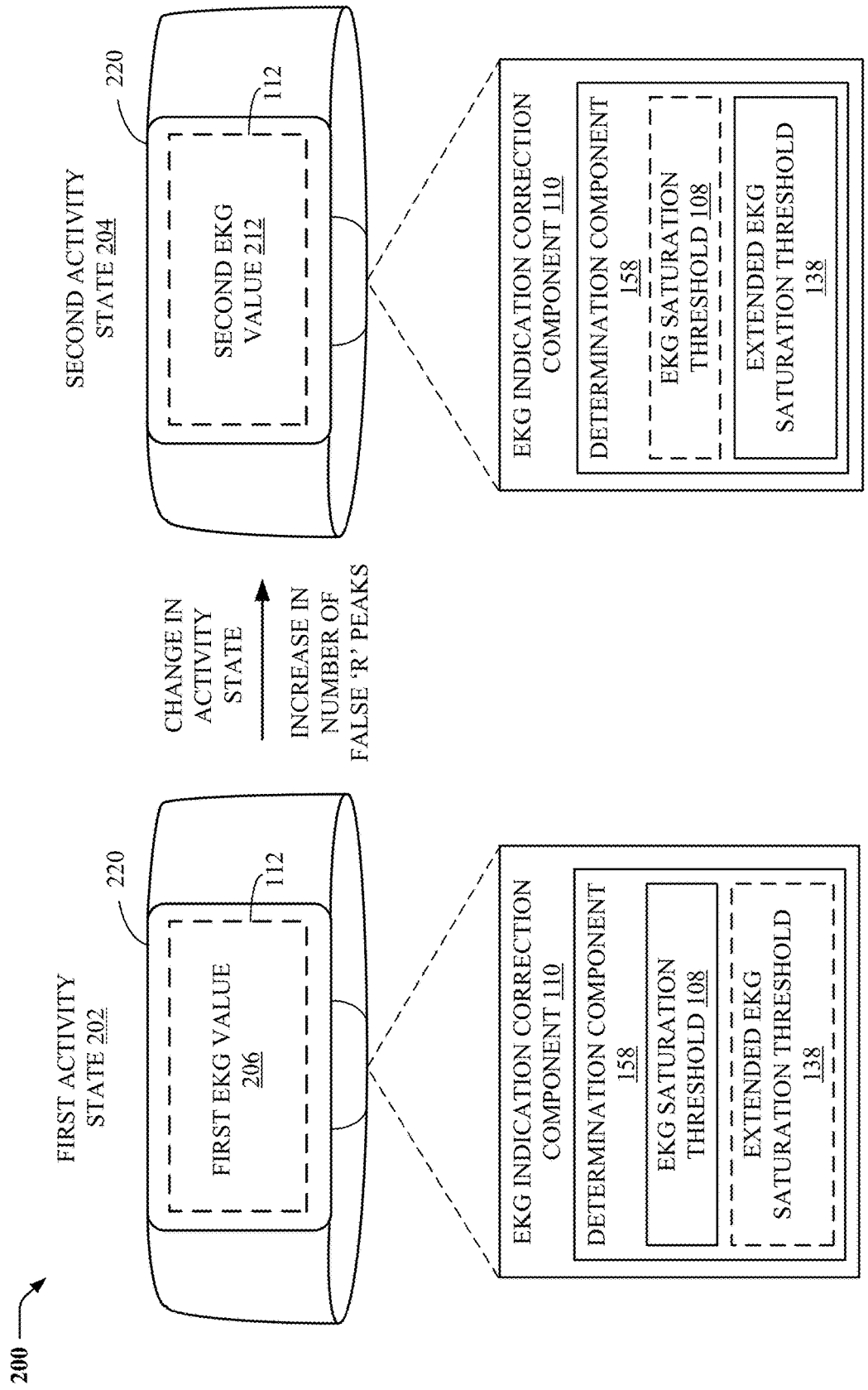
FIG. 2 is a conceptual diagram of EKG determinations at an example wearable electronic device in accordance with some implementations.

Referring now to FIG. 2, a conceptual diagram 200 is shown of an example wearable electronic device 220 displaying EKG values based on the electrical activity of a heart of a user wearing the wearable electronic device 220, in accordance with some implementations. The conceptual diagram 200 illustrates the capability of the wearable electronic device 220 to determine and display two distinct EKG values based on a change in an activity state of the user as detected by the wearable electronic device 220 within, for example, a period of time. Further, the wearable electronic device 220 may be capable of managing an increase in a number of false 'R' wave peaks during an activity state via EKG indication correction component 110. In some implementations, the wearable electronic device 220 may be the same as or similar to electronic device 100 (FIG. 1A). For example, while detecting an EKG indication, the wearable electronic device 220 may be in or otherwise detect a first activity state 202. The first activity state 202 may correspond to or otherwise include sitting, walking, running, etc.

EKG indication correction component 110 may display a first EKG value 206 associated with an unsaturated EKG indication/measurement during the first activity state 202 based on, for instance, at least the implementations described herein with respect to FIGS. 1A and 1B. Specifically, while in the first activity state 202, EKG indication correction component 110 may determine that the EKG saturation threshold 108 has been met after receiving a number of consecutive saturated EKG indications. EKG indication correction component 110 may disregard (e.g., 'zero') subsequent EKG indications exhibiting saturated characteristics (e.g., false 'R' wave peaks) until an unsaturated EKG indication is sampled or detected (e.g., an unsaturated EKG indication corresponding to first EKG value 206). The wearable electronic device 220 may then display the first EKG value 206 on the display 112.

However, a change in activity state may subsequently occur within a period of time. In particular, a user of the wearable electronic device 220 may enter into a second activity state, which may correspond to or otherwise include an activity that is distinct from the first activity state 202 (e.g., different from sitting, walking, running, etc.). For example, the second activity state 204 may be indicative of an increase in activity level resulting in wet or moist conditions (e.g., skin) coming in contact with the wearable electronic device 220, and in particular, the EKG sensor. Such conditions may result in higher conductivity in or around the EKG sensor, which in turn may result in an increase in a number of false 'R' wave peaks detected by the EKG sensor.

As such, to correct such false 'R' wave peaks, which may occur for an extended or prolonged period of time compared to the false 'R' peaks that occurred during the first activity state 202, EKG indication correction component 110 may also determine whether the extended EKG saturation threshold 138 has been met (e.g., as described herein with respect to FIGS. 1A and 1B). EKG indication correction component 110 may zero or skip a number of EKG indications detected after determining that the extended EKG saturation threshold 138 has been met for the extended correction period, irrespective of if the EKG indications are unsaturated. The wearable electronic device 220 may then display the second EKG value 212 associated with a second EKG indication/measurement on the display 112 following an expiration of extended correction period 160.

Figure 3:
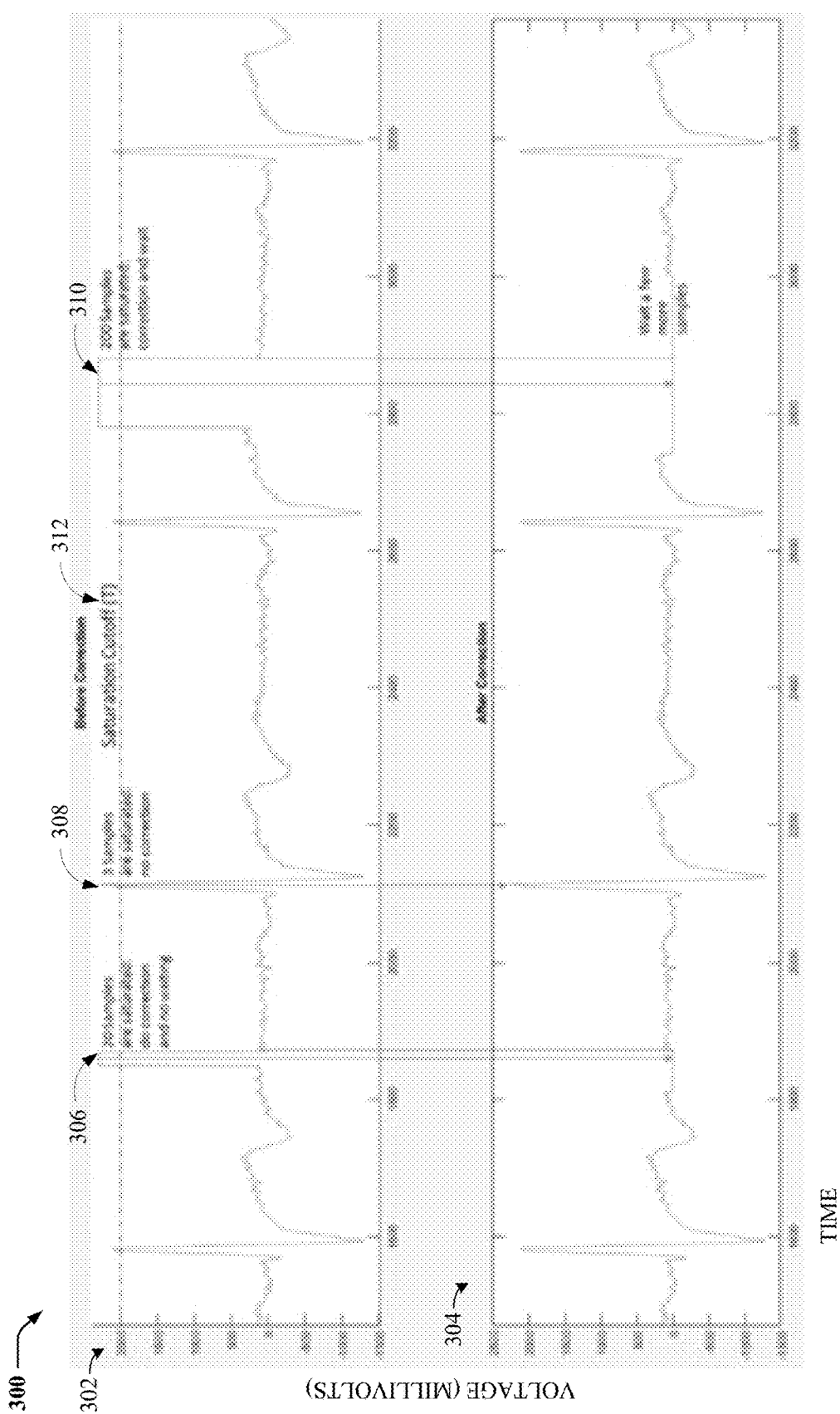
FIG. 3 is a graphical representation of example electrocardiogram (EKG) measurements in accordance with some implementations.

FIG. 3 is an example graphical representation 300 of an original EKG indications/measurement graph 302 before correction and a corrected EKG indications/measurement graph 304 after correction by the EKG indication correction component 110 (FIGS. 1A and 1B). Each graph includes a representation in volts/millivolts over time (in milliseconds/seconds) in accordance with some implementations.

In the original EKG indications/measurement graph 302, a number of saturation events may occur over the course of the measurement duration (e.g., from 0 to 3200 msec).

Between or among these saturation events, there may also be normal EKG events that exhibit saturation conditions. For instance, the EKG indications at 1600 msec, 2500 msec, and 3200 msec exhibit unsaturated characteristics, notably the lack of consecutive false 'R' wave peaks following a real 'R' wave peak. In some implementations, an 'R' wave peak may be indicative of a waveform value (e.g., in millivolts) meeting or exceeding a saturation cutoff (T) 312.

Moreover, for example, during a first saturation event 306, a first number (e.g., 20) of EKG indications (also referred to as EKG samples) may be determined to be saturated (e.g., by EKG indication correction component 110, FIGS. 1A and 1B). Specifically, EKG indication correction component 110 (FIGS. 1A and 1B) may determine that a number of consecutive 'R' wave peaks (e.g., saturation level 156, FIG. 1B) meets or exceeds an EKG saturation threshold 108. Upon determining that a saturation level (e.g., 10 EKG samples) satisfies an EKG saturation threshold 108 (FIG. 1B) (e.g., of 10 saturated EKG samples), some or all of the saturated EKG indications/samples may be corrected (e.g., 'zeroed') by EKG indication correction component 110 (FIGS. 1A and 1B), as shown in the corrected EKG indications/measurement graph 304. That is, not only are those EKG indications/samples that satisfied the EKG saturation threshold 108 (FIG. 1B) 'zeroed', but some or all of the remaining or subsequent saturated EKG indications/samples are also zeroed.

Additionally, in some implementations, during a second saturation event 308, a second number (e.g., 3) of EKG indications/samples may be determined to be saturated (e.g., by EKG indication correction component 110, FIGS. 1A and 1B) when a false 'R' wave peak is detected following a previous 'R' wave peak. However, as the second number of EKG indications/samples may not satisfy the EKG saturation threshold (e.g., of 10 saturated EKG samples), EKG indication correction component 110 (FIGS. 1A and 1B) may not correct (e.g., 'zero') the second number of EKG indications/samples.

Further, in a third saturation event 310, a third number (e.g., 200) of EKG indications/samples may be determined to be saturated (e.g., by EKG indication correction component 110, FIGS. 1A and 1B). In such scenario, as the third number of EKG indications/samples satisfies the EKG saturation threshold (e.g., of 10 saturated EKG samples), a subsequent determination may also be made as to whether the third number of EKG indications/samples satisfies the extended EKG threshold 138 (FIG. 1B). Upon determining that a saturation level satisfies the extended EKG saturation threshold 138 (FIG. 1B), not only may a number of subsequent EKG indications/samples be corrected (e.g., 'zeroed') by EKG indication correction component 110 (FIGS. 1A and 1B), but also a number of unsaturated EKG indications may be corrected so as to allow the EKG readings to stabilize.

Thus, based on the operation of EKG indication correction component 110 on the EKG indications/samples of example original EKG indications/measurements graph 302, EKG indication correction component 110 may generate (or at least store the values of) the example corrected EKG indications/measurement graph 304, thereby reducing or eliminating false 'R' wave peaks.

Figure 4A:
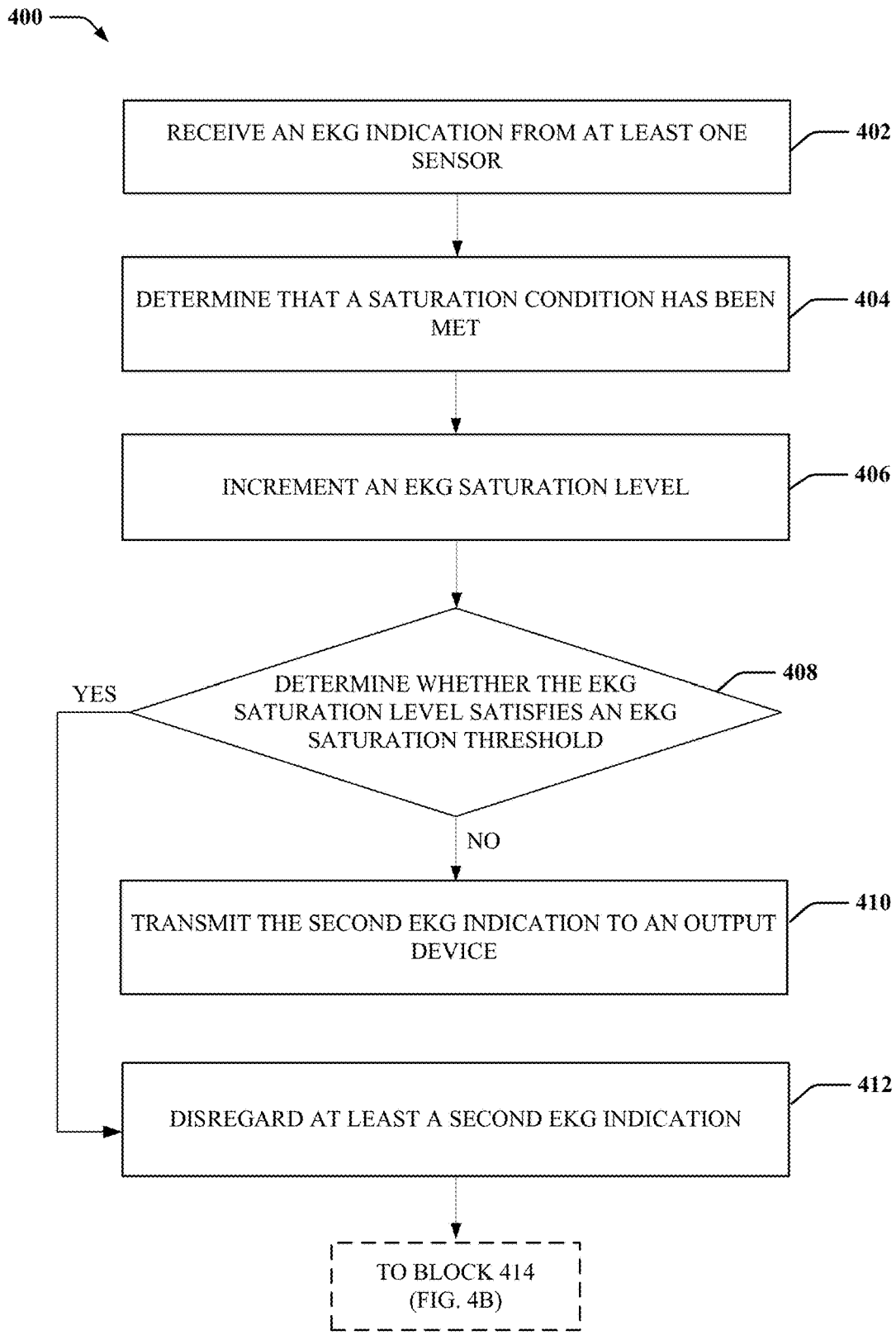
FIGS. 4A and 4B are flow charts of an example of a method of correcting EKG indication saturation in accordance with some implementations.
Figure 4B:
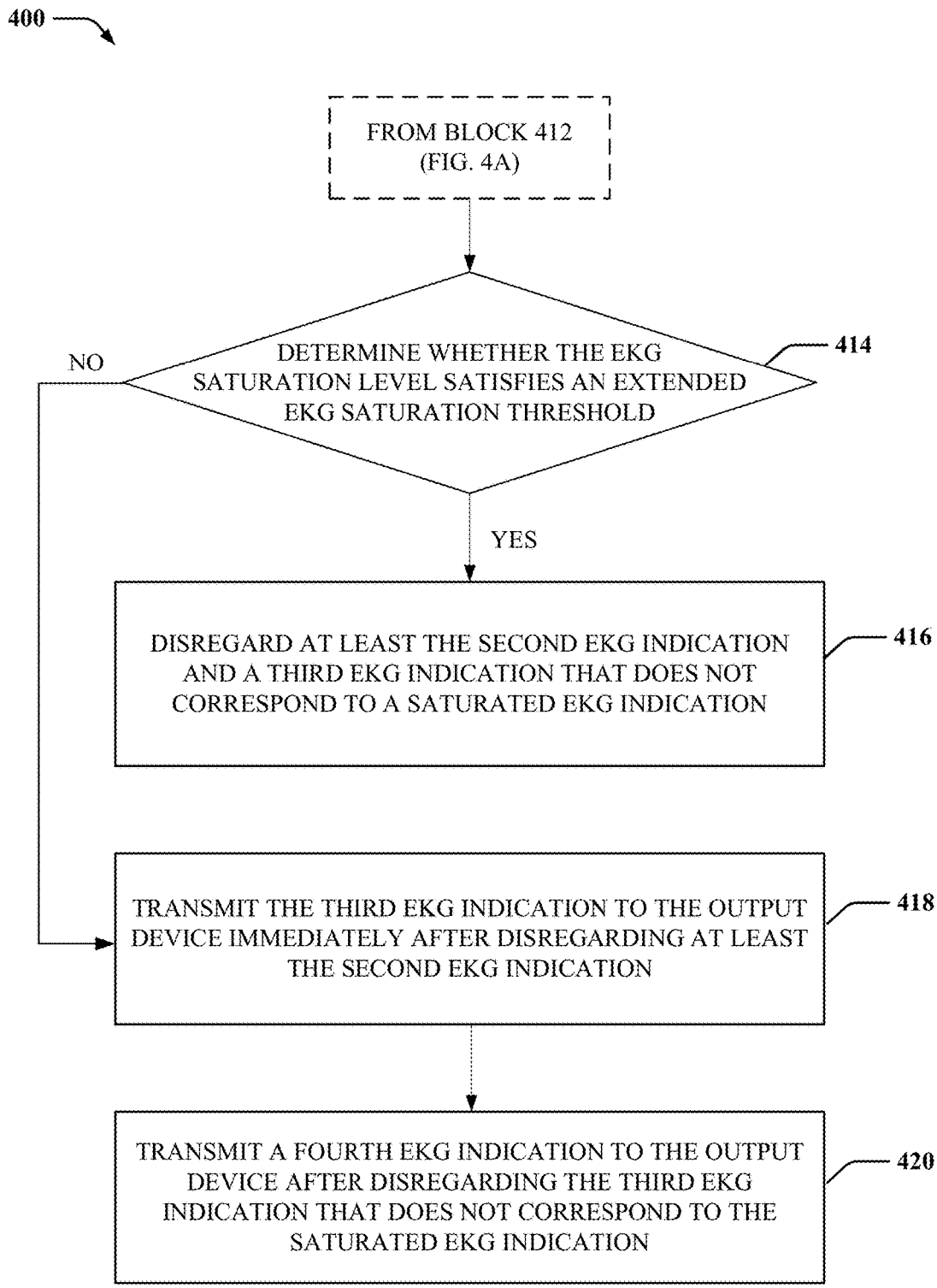

FIGS. 4A and 4B are flow diagrams of an example of a method 400 related to EKG indication saturation correction in accordance with various implementations of the present disclosure. Although the operations described below are presented in a particular order and/or as being performed by an example component, it should be understood that the ordering of the actions and the components performing the actions may be varied, depending on the implementation.

At block 402, method 400 may receive an EKG indication from at least one sensor. For instance, electronic device 100 (FIG. 1A) may execute EKG sensor 136 (e.g., FIG. 1A) to receive the EKG indication (e.g., part of EKG indications 150, FIG. 1B).

Further, at block 404, method 400 may determine that a saturation condition has been met. For example, electronic device 100 (FIG. 1A) may execute EKG indication correction component 110 (FIGS. 1A and 1B) to determine that a saturation condition 154 (FIG. 1B) has been met. In some implementations, determining that the saturation condition 154 (FIG. 1B) has been met includes detecting that the EKG indication includes an 'R' wave peak that follows a previous EKG indication also including an 'R' wave peak.

At block 406, method 400 may increment an EKG saturation level. For instance, electronic device 100 (FIG. 1A) may execute EKG indication correction component 110 (FIGS. 1A and 1B) to increment an EKG saturation level 156 (FIG. 1B) based on a determination that the saturation condition 154 (FIG. 1B) has been met. In some implementations, the EKG saturation level 156 may indicate a number of saturated EKG indications received from the EKG sensor 136 (FIG. 1A).

Moreover, at block 408, method 400 may determine whether the EKG saturation level satisfies an EKG saturation threshold. For example, electronic device 100 (FIG. 1A) may execute EKG indication correction component 110 (FIGS. 1A and 1B) to determine whether the EKG saturation level 156 (FIG. 1B) satisfies an EKG saturation threshold 108 (FIG. 1B). In some implementations, the EKG saturation threshold 108 may correspond to a minimum number of saturated EKG indications sufficient for triggering a correction of at least one EKG indication based on a determination that the minimum number of saturated EKG indications have been met. Further, determining whether the EKG saturation level 156 (FIG. 1B) satisfies the EKG saturation threshold 108 (FIG. 1B) includes determining whether the EKG saturation level 156 (FIG. 1B) meets or exceeds the EKG saturation threshold 108 (FIG. 1B).

Method 400 may proceed to block 410 based on a determination that the EKG saturation level does not satisfy the EKG saturation threshold. Specifically, at block 410, method 400 may transmit the second EKG indication to an output device. For instance, electronic device 100 (FIG. 1A) may execute EKG indication correction component 110 (FIGS. 1A and 1B) to transmit the second EKG indication to display 112 (FIG. 1A).

Otherwise, method 400 may proceed to block 412 based on a determination that the EKG saturation level satisfies the EKG saturation threshold. In particular, at block 412, method 400 may disregard at least a second EKG indication. For example, electronic device 100 (FIG. 1A) may execute EKG indication correction component 110 (FIGS. 1A and 1B) to disregard at least a second EKG indication that is detected and/or received after the EKG indication. In some implementations, disregarding at least the second EKG indication includes indicating a zero EKG value (e.g., 'zeroing') at a time of the second EKG indication.

At block 414, method 400 may determine whether the EKG saturation level satisfies an extended EKG saturation threshold. For instance, electronic device 100 (FIG. 1A) may execute EKG indication correction component 110 (FIGS. 1A and 1B) to determine whether the EKG saturation level 156 (FIG. 1B) satisfies an extended EKG saturation threshold 138 (FIG. 1B). In some implementations, the extended EKG saturation threshold 138 (FIG. 1B) may correspond to an extended number of saturated EKG indications sufficient for triggering a correction of at least one saturated EKG indication and at least one unsaturated EKG indication based on a determination that the extended number of saturated EKG indications have been met. Further, the extended EKG saturation threshold 138 (FIG. 1B) may be greater than the EKG saturation threshold 108 (FIG. 1B).

Method 400 may proceed to block 416 based on a determination that the EKG saturation level satisfies the extended EKG saturation threshold. Specifically, at block 416, method 400 may disregard at least the second EKG indication and a third EKG indication that does not correspond to a saturated EKG indication. For example, electronic device 100 (FIG. 1A) may execute EKG indication correction component 110 (FIGS. 1A and 1B) to disregard (e.g., 'zeroing') at least the second EKG indication and a third EKG indication that does not correspond to a saturated EKG indication. In some implementations, the saturated EKG indication may correspond to a false 'R' wave peak value.

Otherwise, method 400 may proceed to block 418 based on a determination that the EKG saturation level does not satisfy an extended EKG saturation threshold. In particular, at block 418, method 400 may transmit the third EKG indication to the output device immediately after disregarding at least the second EKG indication. For instance, electronic device 100 (FIG. 1A) may execute EKG indication correction component 110 (FIGS. 1A and 1B) to transmit the third EKG indication to the display 112 (FIG. 1A) immediately after disregarding (e.g., 'zeroing') at least the second EKG indication. In some implementations, the third EKG indication may be received after the second EKG indication corresponding to the saturated EKG indication.

At block 420, method 400 may transmit a fourth EKG indication to the output device after disregarding the third EKG indication that does not correspond to the saturated EKG indication. For example, electronic device 100 (FIG. 1A) may execute EKG indication correction component 110 (FIGS. 1A and 1B) to transmit a fourth EKG indication to the display 112 (FIG. 1A) after disregarding the third EKG indication that does not correspond to the saturated EKG indication. In some implementations, the fourth EKG indication may not correspond to the saturated EKG indication.

Figure 5:
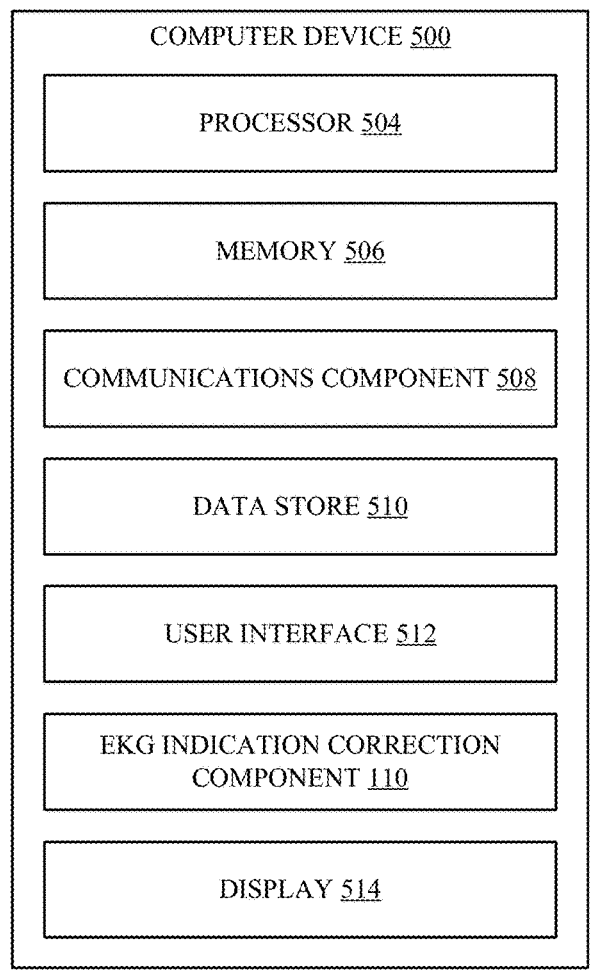
FIG. 5 is a schematic block diagram of an example computer device in accordance with some implementations.

Referring now to FIG. 5, an example computer device 500 includes additional component details as compared to FIGS. 1A and 1B. Computer device 500 may be the same as or similar to or another version of electronic device 100 (FIG. 1A). In one implementation, computer device 500 may include processor 504 for carrying out processing functions associated with one or more of components and functions described herein. Processor 504 can include a single or multiple set of processors or multi-core processors. Moreover, processor 504 can be implemented as an integrated processing system and/or a distributed processing system.

Computer device 500 may further include memory 506, such as for storing local versions of applications being executed by processor 504. Memory 506 can include a type of memory usable by a computer, such as random access memory (RAM), read only memory (ROM), tapes, magnetic discs, optical discs, volatile memory, non-volatile memory, and any combination thereof. Additionally, processor 504 and memory 506 may include and execute EKG indication correction component 110 (FIGS. 1A and 1B).

Further, computer device 502 may include a communications component 508 that provides for establishing and maintaining communications with one or more parties utilizing hardware, software, and services as described herein. Communications component 508 may carry communications between components on computer device 500, as well as between computer device 500 and external devices, such as devices located across a communications network and/or devices serially or locally connected to computer device 500. For example, communications component 508 may include one or more buses, and may further include transmit chain components and receive chain components associated with a transmitter and receiver, respectively, operable for interfacing with external devices.

Additionally, computer device 500 may include a data store 510, which can be any suitable combination of hardware and/or software, that provides for mass storage of information, databases, and programs employed in connection with implementations described herein. For example, data store 510 may be a data repository for EKG saturation threshold 108 (FIG. 1A) and extended EKG saturation threshold 138 (FIG. 1A). In some implementations, computer device 500 may also include display 514 for displaying content.

Computer device 500 may also include a user interface component 512 operable to receive inputs from a user of computer device 500 and further operable to generate outputs for presentation to the user. User interface component 512 may include one or more input devices, including but not limited to a keyboard, a number pad, a mouse, a touch-sensitive display, a navigation key, a function key, a microphone, a voice recognition component, any other mechanism capable of receiving an input from a user, or any combination thereof. Further, user interface component 512 may include one or more output devices, including but not limited to a display, a speaker, a haptic feedback mechanism, a printer, any other mechanism capable of presenting an output to a user, or any combination thereof.

As used in this application, the terms "component," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computer device and the computer device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Furthermore, various implementations are described herein in connection with a device (e.g., electronic device 100 and/or computer device 500), which can be a wired device or a wireless device. A wireless device may be a wearable electronic device, a cellular telephone, a satellite phone, a cordless telephone, a Session Initiation Protocol (SIP) phone, a wireless local loop (WLL) station, a personal digital assistant (PDA), a handheld device having wireless connection capability, a computer device, or other processing devices connected to a wireless modem.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Various implementations or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches may also be used.

The various illustrative logics, logical blocks, and actions of methods described in connection with the embodiments disclosed herein may be implemented or performed with a specially-programmed one of a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computer devices, e.g., a combination of a DSP and a microprocessor, a plurality of microprocessors, one or more microprocessors in conjunction with a DSP core, or any other such configuration. Additionally, at least one processor may comprise one or more components operable to perform one or more of the steps and/or actions described above.

Further, the steps and/or actions of a method or algorithm described in connection with the implementations disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some implementations, the processor and the storage medium may reside in an ASIC. Additionally, the ASIC may reside in a user terminal. In the alternative, the processor and the storage medium may reside as discrete components in a user terminal. Additionally, in some implementations, the steps and/or actions of a method or algorithm may reside as one or any combination or set of codes and/or instructions on a machine readable medium and/or computer readable medium, which may be incorporated into a computer program product.

In one or more implementations, the functions described may be implemented in hardware, software, firmware, or any combination thereof. If implemented in software, the functions may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

While implementations of the present disclosure have been described in connection with examples thereof, it will be understood by those skilled in the art that variations and modifications of the implementations described above may be made without departing from the scope hereof. Other implementations will be apparent to those skilled in the art from a consideration of the specification or from a practice in accordance with implementations disclosed herein.

What is claimed is:

1. A method of resolving electrocardiogram (EKG) indication saturation at an electronic device, comprising:
    receiving an EKG indication from at least one sensor;
    determining that a saturation condition has been met in response to receiving the EKG indication;
    incrementing an EKG saturation level indicating a number of saturated EKG indications received from the at least one sensor based on a determination that the saturation condition has been met;
    determining whether the EKG saturation level satisfies an EKG saturation threshold corresponding to a minimum number of saturated EKG indications sufficient for triggering a correction of at least one EKG indication;
    disregarding at least a second EKG indication in accordance with a determination that the saturation level satisfies the EKG saturation threshold; and
    transmitting the second EKG indication to an output device in accordance with a determination that the saturation level does not satisfy the EKG saturation threshold.

2. The method of claim 1, wherein determining that the saturation condition has been met includes detecting that the EKG indication includes an 'R' peak that follows a previous EKG indication also including an 'R' peak.

3. The method of claim 1, further comprising:
    determining whether the EKG saturation level satisfies an extended EKG saturation threshold that is greater than the EKG saturation threshold; and transmitting a third EKG indication to the output device immediately after disregarding at least the second EKG indication in accordance with a determination that the EKG saturation level does not satisfy the extended EKG saturation threshold; wherein the third EKG indication is received after the second EKG indication corresponding to the saturated EKG indication.

4. The method of claim 3, further comprising:
    disregarding at least the second EKG indication and the third EKG indication that does not correspond to a saturated EKG indication in accordance with a determination that the EKG saturation level satisfies the extended EKG saturation threshold; and transmitting a fourth EKG indication to the output device after disregarding the third EKG indication, the fourth EKG indication not corresponding to the saturated EKG indication.

5. The method of claim 4, wherein the saturated EKG indication corresponds to a false 'R' peak value.

6. The method of claim 3, wherein the extended EKG saturation threshold corresponds to an extended number of saturated EKG indications sufficient for triggering a correction of at least one saturated EKG indication and at least one unsaturated EKG indication.

7. The method of claim 1, wherein disregarding at least the second EKG indication includes indicating a zero EKG value at a time of the second EKG indication.

8. The method of claim 1, wherein the electronic device is a wearable electronic device, the output device corresponds to a display, and the at least one sensor includes an EKG sensor.

9. An electronic device for resolving electrocardiogram (EKG) indication saturation, comprising:
   a memory configured to store data and instructions;
   at least one sensor configured to obtain one or more sensor measurements; and
   a processor in communication with the memory, an output device, and the at least one sensor, wherein the processor is configured to:
      receive an EKG indication from the at least one sensor;
      determine that a saturation condition has been met in response to receiving the EKG indication;
      increment an EKG saturation level indicating a number of saturated EKG indications received from the at least one sensor based on a determination that the saturation condition has been met;
      determine whether the EKG saturation level satisfies an EKG saturation threshold corresponding to a minimum number of saturated EKG indications sufficient for triggering a correction of at least one EKG indication;
      disregard at least a second EKG indication in accordance with a determination that the saturation level satisfies the EKG saturation threshold; and
      transmit the second EKG indication to an output device in accordance with a determination that the saturation level does not satisfy the EKG saturation threshold.

10. The electronic device of claim 9, wherein to determine that the saturation condition has been met, the processor is further configured to detect that the EKG indication includes an 'R' peak that follows a previous EKG indication also including an 'R' peak.

11. The electronic device of claim 9, wherein the processor is further configured to:
   determine whether the EKG saturation level satisfies an extended EKG saturation threshold that is greater than the EKG saturation threshold; and
   transmit a third EKG indication to the output device immediately after disregarding at least the second EKG indication in accordance with a determination that the EKG saturation level does not satisfy the extended EKG saturation threshold;
   wherein the third EKG indication is received after the second EKG indication corresponding to the saturated EKG indication.

12. The electronic device of claim 11, wherein the processor is further configured to:
   disregard at least the second EKG indication and the third EKG indication that does not correspond to a saturated EKG indication in accordance with a determination that the EKG saturation level satisfies the extended EKG saturation threshold; and
   transmit a fourth EKG indication to the output device after disregarding the third EKG indication, the fourth EKG indication not corresponding to the saturated EKG indication.

13. The electronic device of claim 12, wherein the saturated EKG indication corresponds to a false 'R' peak value.

14. The electronic device of claim 11, wherein the extended EKG saturation threshold corresponds to an extended number of saturated EKG indications sufficient for triggering a correction of at least one saturated EKG indication and at least one unsaturated EKG indication.

15. The electronic device of claim 9, wherein to disregard at least the second EKG indication, the processor is further configured to indicate a zero EKG value at a time of the second EKG indication.

16. A non-transitory computer-readable medium storing instructions executable by an electronic device for resolving electrocardiogram (EKG) indication saturation, comprising at least one instruction for causing the electronic device to:
   receive an EKG indication from at least one sensor;
   determine that a saturation condition has been met in response to receiving the EKG indication;
   increment an EKG saturation level indicating a number of saturated EKG indications received from the at least one sensor based on a determination that the saturation condition has been met;
   determine whether the EKG saturation level satisfies an EKG saturation threshold corresponding to a minimum number of saturated EKG indications sufficient for triggering a correction of at least one EKG indication;
   disregard at least a second EKG indication in accordance with a determination that the saturation level satisfies the EKG saturation threshold; and
   transmit the second EKG indication to an output device in accordance with a determination that the saturation level does not satisfy the EKG saturation threshold.

* * * * *